United States Patent [19]

Paspa et al.

[11] Patent Number: 5,509,924
[45] Date of Patent: Apr. 23, 1996

[54] EPICARDIAL STIMULATION ELECTRODE WITH ENERGY DIRECTING CAPABILITY

[75] Inventors: Paul M. Paspa, Santa Clara; Peter A. Altman, Woodside, both of Calif.

[73] Assignee: Ventritex, Inc., Sunnyvale, Calif.

[21] Appl. No.: 226,741

[22] Filed: Apr. 12, 1994

[51] Int. Cl.$^6$ ..................................... A61N 1/05
[52] U.S. Cl. .............................. 607/5; 607/129
[58] Field of Search ..................... 607/129, 119, 607/130, 131, 148, 152, 5

[56] References Cited

U.S. PATENT DOCUMENTS

| | | | |
|---|---|---|---|
| 4,030,509 | 6/1977 | Heilman et al. | 128/419 |
| 4,291,707 | 9/1981 | Heilman et al. | 128/784 |
| 4,314,095 | 2/1982 | Moore et al. | 128/419 |
| 4,774,952 | 10/1988 | Smits | 128/419 |
| 4,817,634 | 4/1989 | Holleman et al. | 128/784 |
| 4,827,932 | 5/1989 | Ideker et al. | 128/419 |
| 4,938,231 | 7/1990 | Milijasevic et al. | 128/784 |
| 4,955,381 | 9/1990 | Way et al. | 607/4 |
| 5,042,463 | 8/1991 | Lekholm | 128/784 |
| 5,044,374 | 9/1991 | Lindemans et al. | 128/784 |
| 5,063,932 | 11/1991 | Dahl et al. | 128/639 |
| 5,107,834 | 4/1992 | Ideker et al. | 607/5 |
| 5,203,348 | 4/1993 | Dahl et al. | 607/129 |
| 5,290,299 | 3/1994 | Fain et al. | 606/142 |
| 5,327,909 | 7/1994 | Kiser et al. | 607/129 |
| 5,391,200 | 2/1995 | KenKnight et al. | 607/129 |
| 5,411,547 | 5/1995 | Causey, III | 607/129 |

OTHER PUBLICATIONS

CPA Cardioverter Defibrillator Product Line Price List Effective Oct. 1, 1987.
"Current Concepts for Selecting the Location, Size and Shape of Defibrillation Electrodes", Ideker, R. E., et al PACE, vol. 14, Feb. 1991, Part I, pp. 227–240.
"Effective Defibrillation in Pigs using Interleaved and Common Phase Sequential Biphasic Shocks", Guse, P. A. et al, PACE, vol. 16, Aug. 1993, pp. 1719–1734.

Primary Examiner—William E. Kamm
Assistant Examiner—Kennedy J. Schaetzle
Attorney, Agent, or Firm—Steven M. Mitchell; M. Elizabeth Bush; Mark J. Meltzer

[57] ABSTRACT

An epicardial defibrillation electrode having a wide insulating border which insulates the heart from the body is disclosed. The wide insulating border forces defibrillation current to flow through the heart without passing through surrounding tissues, thus increasing the current density throughout the heart, to depolarize the majority of the cardiac tissue with a minimum of energy. By increasing defibrillation efficacy in this way, the conductive surface area of each electrode can be decreased, thus allowing room for implantation of a plurality of conductive electrode portions for controlling energy delivery to the heart both spatially and temporally.

24 Claims, 3 Drawing Sheets

EPICARDIAL STIMULATION ELECTRODE WITH ENERGY DIRECTING CAPABILITY

FIELD OF THE INVENTION

The present invention relates generally to cardiac defibrillation devices, and more specifically to an implantable defibrillation electrode which provides a means for directing energy to the heart.

BACKGROUND OF THE INVENTION

Typical epicardial defibrillation leads are sutured directly to the pericardium or epicardium to direct energy through the heart. The electrodes are sized to maximize the amount of energy delivered to heart tissue without shunting current from lead to lead. The lead configuration used most commonly for epicardial placement is one electrode on the anterior (right ventricle) and one on the posterior (left ventricle) of the heart. Epicardial defibrillation electrodes are commonly oval or rectangular shaped assemblies having a conductive element partially embedded in an insulative backing. An example of this type of electrode is disclosed by Heilman in U.S. Pat. No. 4,291,707 which describes a rectangular mesh electrode having decreased exposed metal at the periphery of the electrode to even the current density across the electrode surface. Another example is presented by Holleman in U.S. Pat. No. 4,817,634 wherein a coil electrode is arranged in the shape of concentric ovals, a spiral oval, or a triangle. Other shapes have been described, such as a shoe, a molar, and a skull in U.S. Pat. No. 4,827,932 to Ideker et al., a pair of shorts in U.S. Pat. No. 5,042,463 to Lekholm, and circles and other shapes in U.S. Pat. Nos. 5,063,932 and 4,938,231 to Dahl et al. and Milijasevic et al., respectively. In the above conventional cases, the nonconductive rim is disclosed as being narrow relative to the size of the electrode, at an estimated two to five millimeters in width, and is provided for suturing the electrode to the heart.

A subcutaneous patch electrode with at least a 0.5" border is disclosed in U.S. Pat. No. 5,044;374 to Lindemans et al. According to Lindemans et al., provision of an electrode pad which extends substantially beyond the conductive portion of the electrode is believed to reduce the chance that transthoracic defibrillation shocks applied in the vicinity of the subcutaneously implanted electrode will propagate through the electrode to the defibrillator to which it is attached.

It is desirable to reduce the size of an implantable cardioverter/defibrillator (ICD) in order to improve patient comfort, reduce risk of erosion through the skin, and facilitate pectoral placement. Because the batteries and capacitors account for a large portion of the defibrillator, reducing the defibrillation threshold (DFT), or the amount of energy required to defibrillate the heart, is key to allowing the device size to be reduced. Using less energy to defibrillate has the added benefit of improving patient comfort and reducing trauma to the conduction system of the heart.

SUMMARY OF THE INVENTION

This invention defines a defibrillation electrode for electrical stimulation of the heart which has the ability to deliver energy to the heart while minimizing the energy delivered to surrounding tissue. By limiting energy delivery to only cardiac tissue, the energy required for defibrillation can be minimized, since energy is not wasted on the surrounding tissue. This is accomplished by providing an extended insulative border on an otherwise typical epicardial patch electrode, to prevent current flow to tissues surrounding the heart. Typically, two leads are used on the heart, either on the epicardium, or on the pericardium, or one of each. As used herein, the term "epicardial" will be used to refer to either epicardial (in the pericardial space) or pericardial (on the pericardium, or extrapericardial). When the leads are in position, the heart is generally surrounded by the electrode, with the conductive portion of the electrode located between the nonconductive portion of the electrode and the heart. The extended border may be a continuation of the backing material, or may be an added rim applied after the conductive portion of the electrode is positioned. In the case where the rim is applied later, several rim sizes may be offered to provide optimal fit to the patient's heart. Alternatively, the backing material or rim may be manufactured wider than intended for implant, to be trimmed to fit the heart by the implanting physician.

The rim is of compliant, nonabrasive, biocompatible material, and of sufficient thickness and dielectric strength to provide adequate electrical insulation. The rim may be any shape so that when formed to the heart the heart is partially or fully surrounded by the leads, with the electrode conforming to the outside of the heart. The backing material or rim may be of an elastomeric material and sufficiently thin and compliant that it can stretch and contract with the filling and pumping of the heart. In the preferred embodiment, the backing material is planar. In an alternative embodiment, the rim is nonplanar, such as formed in a cup shape to conform to the heart. Two or more conductive portions may be contained on a single piece of backing material, and may be of opposite polarity, so that only one such device is needed to defibrillate the heart.

The position of the leads and the geometry of the electrode may vary and is not limited by the added rim material. In the preferred embodiment, the conductive portion of the electrode is offset with respect to the insulative border, and is of a different shape than the insulative border, and the rim is not of uniform width. In an alternative embodiment the conductive portion is of the same shape as the insulative border and is centered within it, and the rim is of uniform width.

In an alternative embodiment of the invention, the epicardial electrode includes one or more smaller areas of conductive surface, such as one centimeter in diameter, which is used to more precisely control the potential gradients of shocks delivered to the heart. In such embodiment, the electrodes used in combination in a patient may have the same or different amounts of total exposed conductive surface.

In another alternative embodiment of the invention, an electrode contains two conductive portions of opposite polarity, so that only one such device is required to defibrillate the heart.

In yet another embodiment of the invention, a plurality of conductive portions of each polarity are included on a single electrode. Pulses can be delivered in various sequences between pairs of conductive portions to achieve a low defibrillation threshold.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
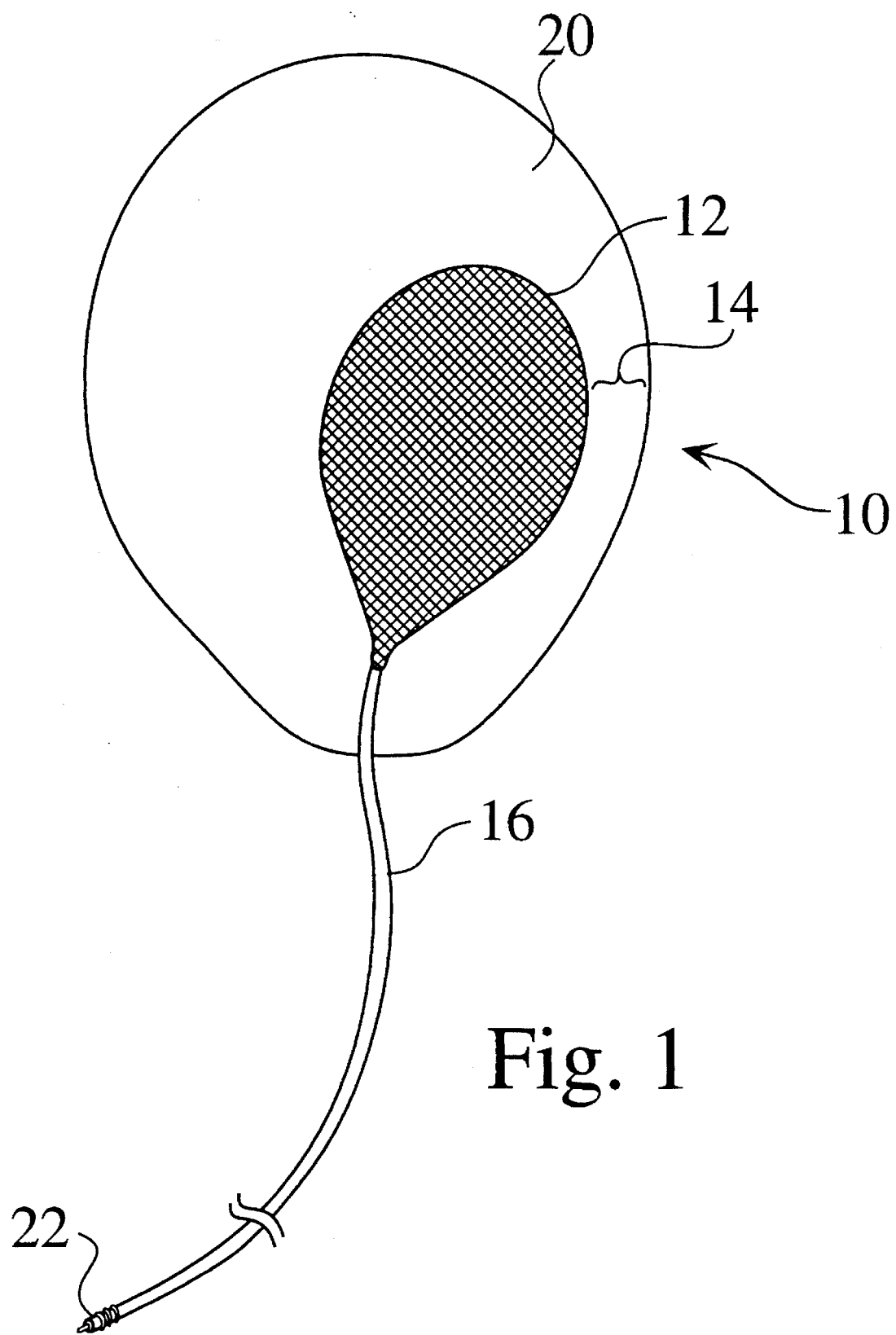
FIG. 1 shows an epicardial defibrillation electrode with a large insulative rim.

FIG. 1 shows an epicardial defibrillation electrode 10 with a conductive area 12, and a nonconductive backing 20, which forms a wide, insulative border, or rim, 14 around the conductive area 12. An insulated lead conductor 16 is electrically attached to conductive area 12 at its electrode end, and is attached to a defibrillation lead connector 22 at its other end. Conventionally designed epicardial defibrillation electrodes have only a small border to suture them in place. The principal advantage of the present invention is that the lead prevents current flow shunting through surrounding body tissues, thereby forcing current through the heart, increasing the current density and energy throughout the heart, to depolarize the greatest amount of cardiac tissue at the lowest possible voltage.

In the preferred embodiment, the conductive portion 12 of the electrode is offset with respect to the insulative border 14, and is of a different shape than the insulative border, and the rim is not of uniform width. In addition, the surface area of the rim 14 is preferably greater than or equal to the surface area of the conductive portion 12. This rim 14 may vary in width from almost 0 centimeters to about 10 centimeters, with an average width of preferably at least 2 centimeters, and as much as 4 to 10 centimeters. In an alternative embodiment the conductive portion is of the same shape as the insulative border and is centered within it, and the rim is of uniform width.

By directing current flow through the heart, the conductive portion of the electrode can be reduced in size to eliminate current shunting while maintaining the lower DFT found with epicardial patch electrodes having larger conductive surface areas. Since conductive materials are usually more rigid than the insulative backing, this reduction in conductive surface area has the added advantage of allowing the electrode to be more easily rolled as required for less invasive implantation through a limited thoracotomy or through a trocar, with or without the aid of a thoracoscope.

In the preferred embodiment, the conductive portion of the electrode is approximately 2 to 3 centimeters in diameter, and is made of small platinum iridium coils partially embedded in polyester reinforced silicone rubber backing, as described for endocardial leads by Mar et al. in U.S. patent application Ser. No. 08/126619 entitled "Flexible Defibrillation Electrode of Improved Construction." Alternatively, many shapes, sizes, and materials are possible for the inventive electrode, including the conventional combination of 38 cm$^2$ elliptical titanium mesh on polyester reinforced elliptical silicone rubber backing.

The electrode can be fixated to the myocardium, or to the pericardium using the "Double Jaw Apparatus for Attaching Implanted Materials to Body Tissue," described by Fain et al. in U.S. Pat. No. 5,290,299, or by using the technique described by Bush et al. in "Implantation of Leads," U.S. Pat. No. 5,249,574, which are both assigned to the assignee of the present application and are incorporated herein by reference. Alternatively, any portion of the rim of the electrode may be sutured in position on the epicardium or pericardium.

When the leads are in position, the heart is generally surrounded by the electrode, with the conductive portion of the electrode located between the nonconductive portion of the electrode and the heart. The extended border may be a continuation of the backing material, or may be an added rim applied after the conductive portion of the electrode is positioned. In the case where the rim is applied later, several rim sizes may be offered to provide optimal fit to the patient's heart. Alternatively, the backing material or rim may be manufactured wider than intended for implant, to be trimmed to fit the heart by the implanting physician.

Unlike electrodes of the prior art, it is not critical that the electrodes do not overlap, since a portion of the insulated border of one electrode may overlap a portion of the insulated border of a second electrode without consequence. It is not intended that the rim seal the heart from surrounding tissue or be without perforations, but the effectiveness of the rim for directing energy to the heart generally increases with increasing coverage.

Figure 2:
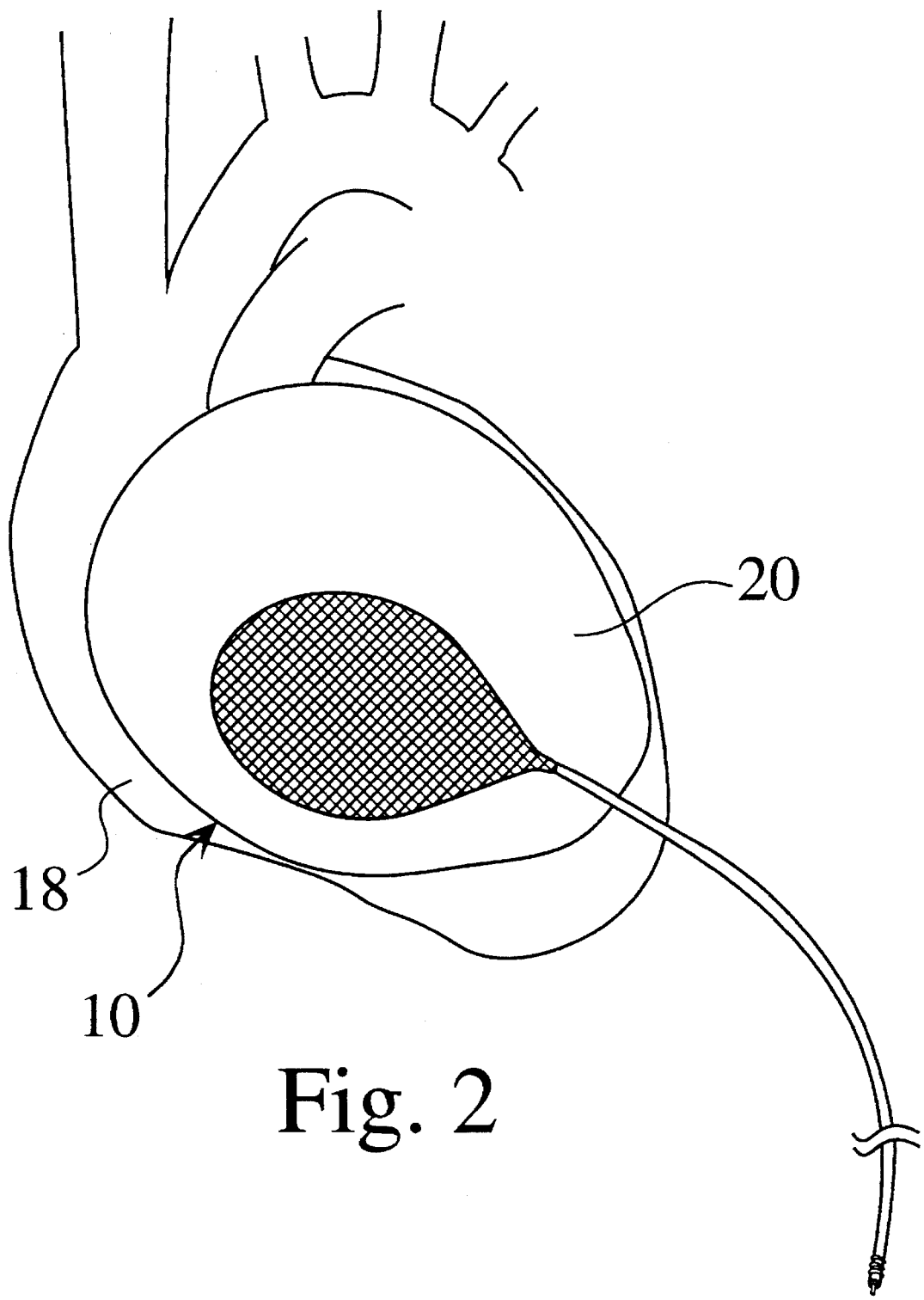
FIG. 2 shows an epicardial defibrillation electrode in position on the heart.

FIG. 2 shows epicardial defibrillation electrode 10 in position on the heart 18. The nonconductive backing 20 is intended to extend so that the whole electrode 10 covers approximately half of the heart. When implanted in pairs the leads conduct energy to the heart and minimize the flow of energy away to the surrounding tissue. This reduces the energy required from the defibrillator to defibrillate the heart.

The electrode or electrode pair may also be used in conjunction with one or more transvenous electrodes, such as a right ventricular or superior vena cava electrode, a conventional epicardial electrode, or a subcutaneous electrode. When only one electrode of this invention is used with a transvenous electrode, approximately half of the heart is insulated from the body. The insulative backing may be positioned such that the body is selectively insulated from the heart; that is, it may not be necessary to completely surround the heart with insulation, but merely to insulate the portion where current flows to the adjacent body tissues.

Figure 3:
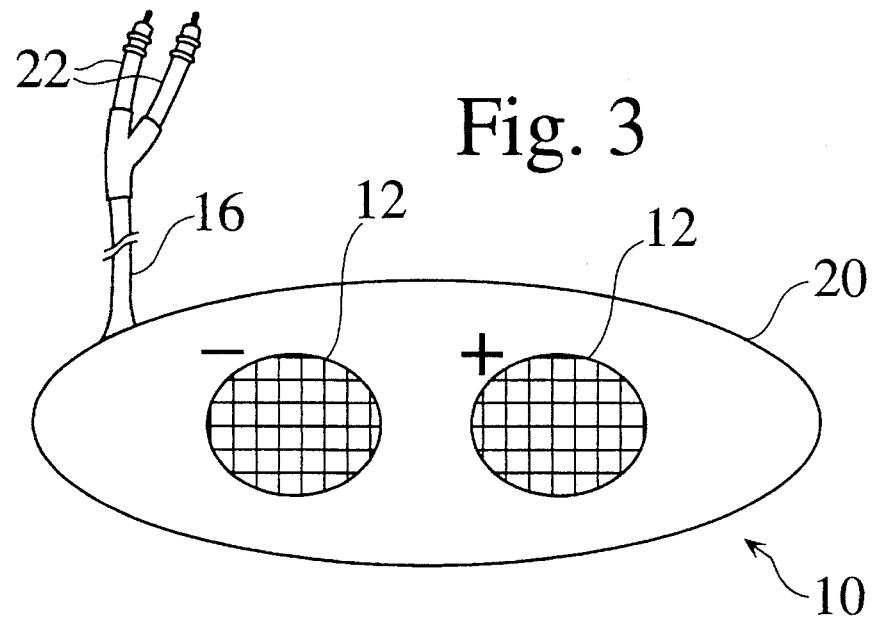
FIG. 3 shows a defibrillation lead having two conductive portions of opposite polarity.

FIG. 3 shows an alternative embodiment of a defibrillation lead of the invention having two conductive portions 12 of opposite polarity. Only one device of this type is necessary to defibrillate the heart. In the preferred embodiment, the conductive portions 12 are approximately 2 to 3 centimeters in diameter, and are spaced apart in order to achieve proper placement on the heart, with one generally on the left ventricular apex, and the other higher up on the right ventricle near the right atrium. Two defibrillation lead connectors 22 are shown, with one connected to each conductive portion 12. Alternatively, the conductive portions 12 may each be connected to a separate pole on a multipolar connector. As used herein, the term "connector" refers to either a unipolar defibrillation lead connector or to a pole (in the form of a pin, ring, or the like) on a multipolar defibrillation lead connector.

Figure 4:
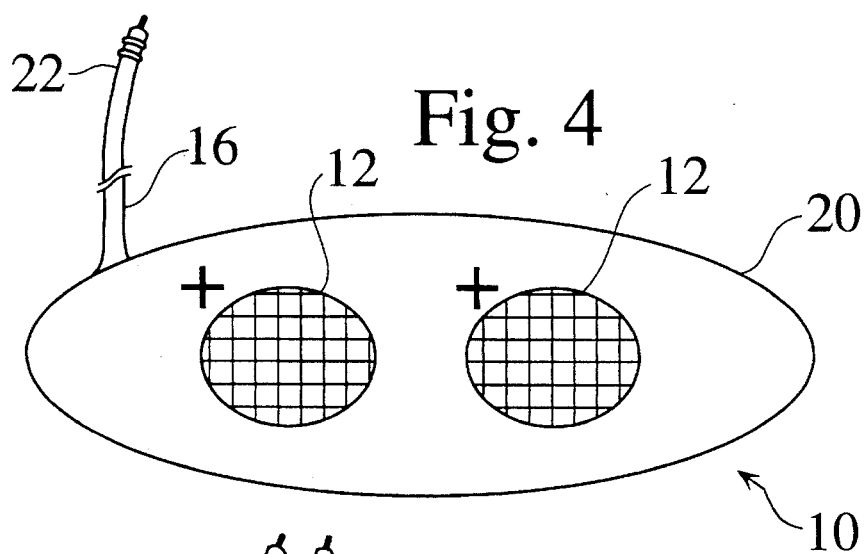
FIG. 4 shows a defibrillation lead having two conductive portions of the same polarity.

FIG. 4 shows a defibrillation lead having two conductive portions 12 of the same polarity. This electrode configuration may be used for directing current to specific regions of the heart, either simply by strategic positioning of the conductive portions on the heart, or by sequential pulsing of the two different portions, or by delivering more current through one portion than through the other.

FIG. 4 shows only one connector which is used to connect to both conductive portions to the implantable defibrillator. However, in the case of sequential pulsing of the two different portions, a separate defibrillation lead connector 22 is required for each conductive portion. In the case of delivering more current through one portion than through the other, different amounts of current may be delivered through separate defibrillation lead connectors 22. Alternatively, a single lead connector may be used with the conductive portions 12 connected in series, with more current flowing through the first conductive portion than through the second conductive portion. This effect can be increased by increasing the resistance separating the first and second conductive portions. Other arrangements are possible to achieve this effect. The polarity of multiple electrodes may be controlled by telemetrically switching the switches in the pulse generator.

Figure 5:
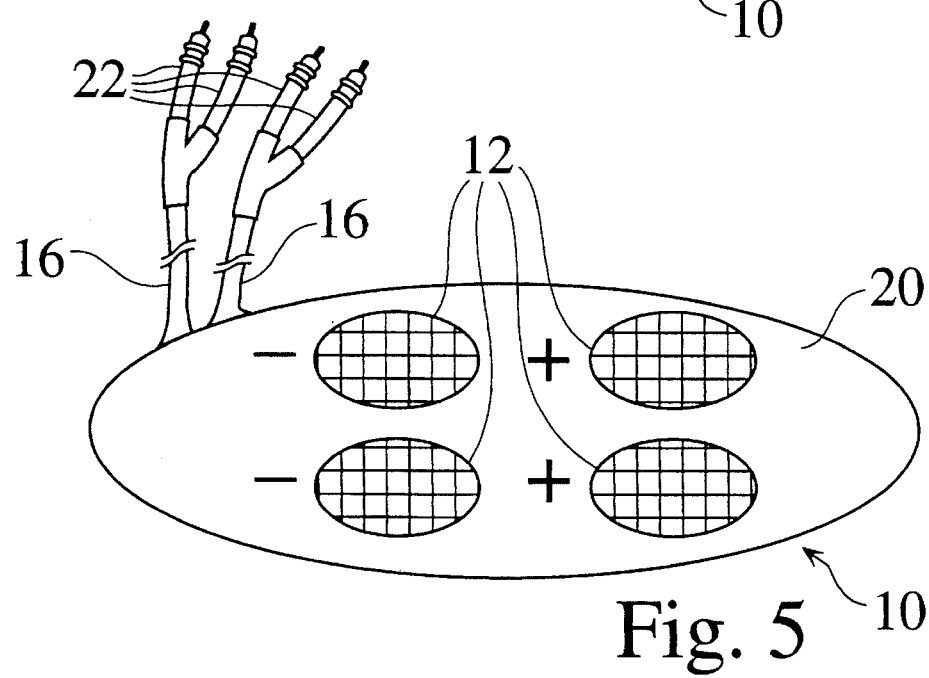
FIG. 5 shows a defibrillation lead having several conductive portions of same and opposite polarity.

FIG. 5 shows a defibrillation lead having two conductive portions 12 of a first polarity and two conductive portions 12 of the opposite polarity. By taking advantage of the current directing properties of the insulative backing 20, smaller conductive portions 12, when properly placed, can be more effective than the larger electrodes of the prior art. Such a device may be used for delivering a series of pulses on different axes of the heart, such as in the manner described by Guse et al. in "*Effective Defibrillation in Pigs Using Interleaved and Common Phase Sequential Biphasic Shocks,*" PACE, vol. 16, Aug. 1993, pp. 1719–1734. In this article, various electrode/waveform configurations were studied to determine their defibrillation efficacy. Some of the more efficacious combinations included sequential biphasic (biphasic shock to a first pair of electrodes, followed by a biphasic shock to a second pair), interleaved biphasic (monophasic shock to a first pair of electrodes, monophasic shock to a second pair, opposite phased shock to the first pair, opposite phased shock to the second pair), and common phase sequential biphasic (monophasic shock to a first pair of electrodes, monophasic shock to a second pair, and opposite phased shock to both pair of electrodes). In order to deliver sequential pulses, separate defibrillation lead connectors 22 are required to each conductive portion 12 desired to be pulsed separately. As shown in FIG. 5, four conductive portions 12 and four corresponding defibrillation lead connectors 22 are shown. Alternatively, only two or three defibrillation connectors may be used if sequential pulsing is not desired for all four conductive portions 12. The insulative backing increases the efficacy of a properly placed electrode, thereby allowing electrodes of smaller conductive area to be used.

It should be understood that various alternatives to the embodiments of the invention described herein may be employed in practicing the invention. For example, the invention may be used for low voltage antitachycardia pacing. It is thus intended that the following claims define the scope of the invention and that structures and methods within the scope of these claims and their equivalents be covered thereby.

What is claimed is:

1. An implantable epicardial cardiac stimulation electrode for delivering defibrillation energy to a patient's heart comprising:

an insulative backing having an outer periphery;

a conductive portion on one surface of said insulative backing and having an outer edge located away from said insulative backing outer periphery by an amount capable of shielding said patient's body from at least a portion of said defibrillation energy; and wherein said conductive portion outer edge is spaced from said insulative backing outer periphery by an average of at least two centimeters.

2. The electrode of claim 1, wherein the spacing between said conductive portion outer edge and said insulative backing outer periphery is an average of between about 4 centimeters and 10 centimeters.

3. The electrode of claim 1, wherein said insulative backing is adapted to be trimmed to fit said patient's heart for optimizing said shielding of said patient's body from said defibrillation energy prior to implantation in said patient.

4. The electrode of claim 1, wherein said insulative backing is nonplanar.

5. The electrode of claim 1, wherein said insulative backing comprises an elastomeric material which is sufficiently compliant to stretch and contract with heart motion.

6. The electrode of claim 1, wherein said insulative backing is nonconcentric with respect to said conductive portion.

7. An implantable epicardial cardiac stimulation electrode comprising: an insulative backing having an outer periphery and upper and lower surfaces;

a conductive material mounted to at least one portion of said lower surface of said insulative backing and defining the inner border of a rim of said insulative backing not covered by said conductive material on said insulative backing lower surface;

said rim having a surface area equal to or greater than the surface area of said conductive material; and wherein said conductive material is spaced from said insulative backing outer periphery by an average of at least two centimeters.

8. The electrode of claim 7, wherein said conductive material is mounted to first and second portions of said lower surface of said insulative backing; and wherein said conductive material in said first portion and said conductive material in said second portion are both coupled to the same pole of a voltage source during cardiac stimulation.

9. The electrode of claim 8, wherein said first conductive portion is electrically coupled to a first defibrillation lead connector, and said second conductive portion is electrically coupled to a second defibrillation lead connector.

10. The electrode of claim 8, wherein said first and second conductive portions are electrically coupled to a single defibrillation lead connector.

11. An implantable epicardial cardiac stimulation electrode comprising;

an insulative backing having an outer periphery and upper and lower surfaces;

a conductive material mounted to at least one portion of said lower surface of said insulative backing and defining the inner border of a rim of said insulative backing not covered by said conductive material on said insulative backing lower surface; and said rim having a surface area equal to or greater than the surface area of said conductive material;

wherein said conductive material is mounted to first and second portions of said lower surface of said insulative backing, said two portions being separated by at least two centimeters; and wherein said conductive material in said first portion and said conductive material in said second portion are coupled to opposite poles of a voltage source during cardiac stimulation.

12. An implantable epicardial cardiac stimulation electrode comprising:

an insulative backing having an outer periphery and upper and lower surfaces;

a conductive material mounted to at least one portion of said lower surface of said insulative backing and defining the inner border of a rim of said insulative backing not covered by said conductive material on said insulative backing lower surface; and said rim having a surface area equal to or greater than the surface area of said conductive material;

wherein said conductive material is mounted to at least a first, a second, and a third portion of said lower surface of said insulative backing; and wherein said conductive material in said first portion and said conductive material in said second portion are both coupled to the same pole of a voltage source and said conductive material in said third portion is coupled to the opposite pole of said voltage source during cardiac stimulation.

13. The electrode of claim 12, wherein said first conductive portion is electrically coupled to a first defibrillation lead connector, said second conductive portion is electrically coupled to a second defibrillation lead connector, and said third conductive portion is electrically coupled to a third defibrillation lead connector.

14. An implantable cardiac stimulation system including a pulse generator for generating defibrillation energy, said pulse generator being electrically connected to an epicardial lead having a lead connector, an insulated conductor, and an electrode, said electrode comprising:

an insulative backing having an outer periphery;

a conductive portion having an outer edge, said conductive portion being mounted to one surface of said insulative backing, and said conductive portion outer edge being spaced from said insulative backing outer periphery by an amount capable of shielding the body from said defibrillation energy; and wherein said conductive portion outer edge is spaced from said insulative backing outer periphery by an average of at least two centimeters.

15. The implantable cardiac stimulation system of claim 14, and further comprising an endocardial right ventricular defibrillation lead.

16. The implantable cardiac stimulation system of claim 14, and further comprising a superior vena cava defibrillation lead.

17. The implantable cardiac stimulation system of claim 14, and further including a second epicardial defibrillation lead.

18. The implantable cardiac stimulation system of claim 14, and further comprising a subcutaneous defibrillation lead.

19. The implantable cardiac stimulation system of claim 14 wherein the surface area of said backing material between said conductive portion outer edge and said insulative backing outer periphery is greater than or equal to the surface area of said conductive portion.

20. An implantable cardiac stimulation system including a pulse generator, said pulse generator electrically attached to an epicardial lead having a lead connector, an insulated conductor, and an electrode, said electrode comprising:

a conductive material for implantation on a patient's heart; and an insulative backing for application onto said conductive material following implantation of said conductive material onto said patient's heart, such that a portion of said insulative backing is in contact with said conductive material, said conductor material defining the inner border of a rim of said insulative backing not covered by said conductive material, said rim having a surface area equal to at least the surface area of said conductive material, and wherein said conductive material is spaced from said insulative backing outer periphery by an average of at least two centimeters.

21. The implantable cardiac stimulation system of claim 20, and further comprising an endocardial right ventricular defibrillation lead.

22. The implantable cardiac stimulation system of claim 20, and further comprising a superior vena cava defibrillation lead.

23. The implantable cardiac stimulation system of claim 20, and further including a second epicardial defibrillation lead.

24. The implantable cardiac stimulation system of claim 20, and further comprising a subcutaneous defibrillation lead.

* * * * *